(12) United States Patent
Biggie et al.

(10) Patent No.: US 8,083,712 B2
(45) Date of Patent: Dec. 27, 2011

(54) FLAT-HOSE ASSEMBLY FOR WOUND DRAINAGE SYSTEM

(75) Inventors: Lydia B. Biggie, Lighthouse Point, FL (US); John A. Dawson, Milton, FL (US)

(73) Assignee: Neogen Technologies, Inc., Coral Springs, FL (US)

( * ) Notice: Subject to any disclaimer, the term of this patent is extended or adjusted under 35 U.S.C. 154(b) by 1226 days.

(21) Appl. No.: 11/725,680

(22) Filed: Mar. 20, 2007

(65) Prior Publication Data
US 2008/0271804 A1 Nov. 6, 2008

(51) Int. Cl.
*A61M 1/06* (2006.01)
(52) U.S. Cl. ......................................................... 604/73
(58) Field of Classification Search ..................... 604/73
See application file for complete search history.

(56) References Cited

U.S. PATENT DOCUMENTS

| | | |
|---|---|---|
| 765,746 A | 7/1904 | Miner |
| 843,674 A | 2/1907 | Funk |
| 1,355,679 A | 10/1920 | McConnell |
| 1,355,846 A | 10/1920 | Bannells |
| 1,385,346 A | 7/1921 | Taylor |
| 2,232,254 A | 2/1941 | Morgan |
| 2,280,915 A | 4/1942 | Johnson |
| 2,338,339 A | 1/1944 | Mere et al. |
| 2,547,758 A | 4/1951 | Keeling |
| 2,969,057 A | 1/1961 | Simmons |
| 3,026,526 A | 3/1962 | Montrose |
| 3,026,874 A | 3/1962 | Stevens |
| 3,042,041 A | 7/1962 | Jascalevich |
| 3,367,332 A | 2/1968 | Groves |
| 3,478,736 A | 11/1969 | Roberts et al. |
| 3,481,326 A | 12/1969 | Schamblin |
| 3,486,504 A | 12/1969 | Austin, Jr. |
| 3,520,300 A | 7/1970 | Flower, Jr. |
| 3,568,675 A | 3/1971 | Harvey |
| 3,572,340 A | 3/1971 | Lloyd et al. |
| 3,610,238 A | 10/1971 | Rich, Jr. |
| 3,648,692 A | 3/1972 | Wheeler |
| 3,682,180 A | 8/1972 | McFarlane |
| 3,809,087 A | 5/1974 | Lewis, Jr. |

(Continued)

FOREIGN PATENT DOCUMENTS

DE 561757 10/1932

(Continued)

OTHER PUBLICATIONS

Arturson, Gosta M., "The Pathophysiology of Severe Thermal Injury," JBCR, Mar./Apr. 1985, 6(2):129-146.

(Continued)

*Primary Examiner* — Nicholas Lucchesi
*Assistant Examiner* — Diva Ranade
(74) *Attorney, Agent, or Firm* — Nixon Peabody LLP

(57) ABSTRACT

A flat-hose assembly has a proximal end and a distal end adapted for use with a negative pressure wound drainage system. The flat-hose assembly comprises a top layer, a bottom layer, and a filter layer. The bottom layer forms an opening at the distal end of the flat-hose assembly to allow exudates of a wound to flow into the flat-hose assembly. The filter layer is disposed between the top layer and the bottom layer. The top and bottom layer form a seal area along a periphery of the top layer and the bottom layer to seal the filter layer therebetween.

18 Claims, 5 Drawing Sheets

U.S. PATENT DOCUMENTS

| | | |
|---|---|---|
| 3,826,254 A | 7/1974 | Mellor |
| 3,874,387 A | 4/1975 | Barbieri |
| 3,896,810 A | 7/1975 | Akiyama |
| 3,908,664 A | 9/1975 | Loseff |
| 3,954,105 A | 5/1976 | Nordby et al. |
| 3,993,080 A | 11/1976 | Loseff |
| RE29,319 E | 7/1977 | Nordby et al. |
| 4,080,970 A | 3/1978 | Miller |
| 4,096,853 A | 6/1978 | Weigand |
| 4,112,947 A | 9/1978 | Nehring |
| 4,139,004 A | 2/1979 | Gonzalez, Jr. |
| 4,149,541 A | 4/1979 | Gammons et al. |
| 4,165,748 A | 8/1979 | Johnson |
| 4,169,563 A | 10/1979 | Leu |
| 4,172,455 A | 10/1979 | Beaussant |
| 4,182,343 A | 1/1980 | Inaba |
| 4,224,945 A | 9/1980 | Cohen |
| 4,250,882 A | 2/1981 | Adair |
| 4,261,363 A | 4/1981 | Russo |
| 4,275,721 A | 6/1981 | Olson |
| 4,297,995 A | 11/1981 | Golub |
| 4,333,468 A | 6/1982 | Geist |
| 4,373,519 A | 2/1983 | Errede |
| 4,382,441 A | 5/1983 | Svedman |
| 4,392,853 A | 7/1983 | Muto |
| 4,419,097 A | 12/1983 | Rowland |
| 4,468,227 A | 8/1984 | Jensen |
| 4,469,092 A | 9/1984 | Marshall et al. |
| 4,475,909 A | 10/1984 | Eisenberg |
| 4,480,638 A | 11/1984 | Schmid |
| 4,525,166 A | 6/1985 | Leclerc |
| 4,527,064 A | 7/1985 | Anderson |
| 4,533,352 A | 8/1985 | Van Beek et al. |
| 4,543,100 A | 9/1985 | Brodsky |
| 4,551,139 A | 11/1985 | Plaas et al. |
| 4,553,967 A * | 11/1985 | Ferguson et al. ............. 604/317 |
| 4,569,348 A | 2/1986 | Hasslinger |
| 4,571,520 A | 2/1986 | Saito et al. |
| 4,573,965 A | 3/1986 | Russo |
| 4,578,065 A | 3/1986 | Habib |
| 4,605,399 A | 8/1986 | Weston et al. |
| 4,608,041 A | 8/1986 | Nielsen |
| 4,624,656 A | 11/1986 | Clark et al. |
| 4,640,688 A | 2/1987 | Hauser |
| 4,733,659 A | 3/1988 | Edenbaum et al. |
| 4,743,232 A | 5/1988 | Kruger |
| 4,759,354 A | 7/1988 | Quarfoot |
| 4,764,167 A | 8/1988 | Tu |
| 4,765,316 A | 8/1988 | Marshall |
| 4,775,909 A | 10/1988 | Inoue et al. |
| 4,778,456 A | 10/1988 | Lokken |
| 4,813,094 A | 3/1989 | Krotine |
| 4,820,265 A | 4/1989 | DeSatnick et al. |
| 4,820,284 A | 4/1989 | Hauri |
| 4,834,110 A | 5/1989 | Richard |
| 4,836,192 A | 6/1989 | Abbate |
| 4,838,883 A | 6/1989 | Matsuura |
| 4,840,187 A | 6/1989 | Brazier |
| 4,851,545 A | 7/1989 | Song et al. |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,917,112 A | 4/1990 | Kalt |
| 4,919,654 A | 4/1990 | Kalt |
| 4,921,492 A * | 5/1990 | Schultz et al. ................ 604/315 |
| 4,925,447 A | 5/1990 | Rosenblatt |
| 4,931,519 A | 6/1990 | Song et al. |
| 4,936,834 A | 6/1990 | Beck et al. |
| 4,941,882 A | 7/1990 | Ward et al. |
| 4,953,565 A | 9/1990 | Tachibana et al. |
| 4,969,880 A | 11/1990 | Zamierowski |
| 4,969,881 A | 11/1990 | Viesturs |
| 4,985,019 A | 1/1991 | Michelson |
| 5,035,884 A | 7/1991 | Song et al. |
| 5,037,397 A | 8/1991 | Kalt et al. |
| 5,045,075 A | 9/1991 | Ersek |
| 5,086,764 A | 2/1992 | Gilman |
| 5,100,396 A | 3/1992 | Zamierowski |
| 5,106,362 A | 4/1992 | Gilman |
| 5,113,871 A | 5/1992 | Viljanto et al. |
| 5,149,331 A | 9/1992 | Ferdman et al. |
| 5,228,431 A | 7/1993 | Giarretto |
| 5,240,862 A | 8/1993 | Koenhen et al. |
| 5,261,893 A | 11/1993 | Zamierowski |
| 5,279,010 A | 1/1994 | Ferrand et al. |
| 5,298,015 A | 3/1994 | Komatsuzaki et al. |
| 5,358,494 A | 10/1994 | Svedman |
| 5,370,610 A | 12/1994 | Reynolds |
| D364,679 S | 11/1995 | Heaton et al. |
| 5,527,293 A | 6/1996 | Zamierowski |
| 5,540,412 A | 7/1996 | Doll |
| 5,549,584 A * | 8/1996 | Gross ............................ 604/313 |
| 5,618,275 A | 4/1997 | Bock |
| 5,624,419 A | 4/1997 | Ersek et al. |
| 5,636,643 A | 6/1997 | Argenta et al. |
| 5,643,229 A | 7/1997 | Sinaiko |
| 5,645,081 A | 7/1997 | Argenta et al. |
| 5,656,588 A | 8/1997 | Zaloga et al. |
| 5,664,270 A | 9/1997 | Bell et al. |
| 5,678,564 A | 10/1997 | Lawrence et al. |
| 5,685,859 A | 11/1997 | Kornerup |
| 5,686,303 A | 11/1997 | Korman |
| 5,840,049 A | 11/1998 | Tumey et al. |
| D406,899 S | 3/1999 | Cottle |
| 5,891,111 A | 4/1999 | Ismael |
| 5,906,016 A | 5/1999 | Ferrand et al. |
| 5,911,222 A | 6/1999 | Lawrence et al. |
| 5,914,264 A | 6/1999 | Korman |
| 5,921,972 A | 7/1999 | Skow |
| 5,926,884 A | 7/1999 | Biggie et al. |
| 5,931,797 A | 8/1999 | Tumey et al. |
| 6,056,730 A | 5/2000 | Greter |
| 6,071,267 A | 6/2000 | Zamierowski |
| 6,102,935 A | 8/2000 | Harlan et al. |
| 6,102,936 A | 8/2000 | Augustine et al. |
| 6,117,111 A | 9/2000 | Fleischmann |
| D434,150 S | 11/2000 | Tumey et al. |
| 6,142,982 A | 11/2000 | Hunt et al. |
| 6,174,306 B1 | 1/2001 | Fleischmann |
| 6,200,195 B1 | 3/2001 | Furuno et al. |
| 6,203,563 B1 | 3/2001 | Fernandez |
| 6,290,685 B1 | 9/2001 | Insley et al. |
| 6,299,593 B1 | 10/2001 | Wakabayashi |
| 6,345,623 B1 | 2/2002 | Heaton et al. |
| 6,375,240 B1 | 4/2002 | Lindberg |
| 6,387,065 B1 | 5/2002 | Tumey |
| 6,398,767 B1 | 6/2002 | Fleischmann |
| 6,406,447 B1 * | 6/2002 | Thrash et al. ................. 601/160 |
| 6,420,622 B1 | 7/2002 | Johnston et al. |
| 6,458,109 B1 | 10/2002 | Henley et al. |
| 6,468,237 B1 | 10/2002 | Lina |
| 6,493,568 B1 | 12/2002 | Bell et al. |
| 6,500,112 B1 | 12/2002 | Khouri |
| D469,175 S | 1/2003 | Hall et al. |
| D469,176 S | 1/2003 | Hall et al. |
| 6,551,280 B1 | 4/2003 | Knighton et al. |
| 6,553,998 B2 | 4/2003 | Heaton et al. |
| D475,132 S | 5/2003 | Randolph |
| D475,134 S | 5/2003 | Randolph |
| 6,557,704 B1 | 5/2003 | Randolph |
| 6,592,889 B1 | 7/2003 | Stout et al. |
| D478,659 S | 8/2003 | Hall et al. |
| 6,620,132 B1 | 9/2003 | Skow |
| 6,626,891 B2 | 9/2003 | Ohmstede |
| 6,641,527 B2 | 11/2003 | Khouri |
| 6,641,575 B1 | 11/2003 | Lonky |
| 6,663,610 B1 | 12/2003 | Thompson et al. |
| 6,685,681 B2 | 2/2004 | Lockwood et al. ........... 604/305 |
| 6,695,823 B1 | 2/2004 | Lina et al. |
| 6,752,794 B2 | 6/2004 | Lockwood et al. |
| 6,755,807 B2 | 6/2004 | Risk et al. |
| 6,764,462 B2 | 7/2004 | Risk, Jr. et al. ................. 604/67 |
| 6,800,074 B2 | 10/2004 | Henley et al. ................. 604/319 |
| 6,824,533 B2 | 11/2004 | Risk, Jr. et al. ............... 604/319 |

| | | | |
|---|---|---|---|
| 6,855,135 B2 * | 2/2005 | Lockwood et al. | 604/313 |
| 7,022,113 B2 | 4/2006 | Lockwood et al. | 604/313 |
| 7,198,046 B1 | 4/2007 | Argenta et al. | 128/897 |
| 7,216,651 B2 | 5/2007 | Argenta et al. | 128/897 |
| 7,338,482 B2 * | 3/2008 | Lockwood et al. | 604/543 |
| 7,794,438 B2 * | 9/2010 | Henley et al. | 604/304 |
| 2001/0029956 A1 | 10/2001 | Argenta et al. | |
| 2002/0082567 A1 | 6/2002 | Lockwood et al. | |
| 2002/0115952 A1 | 8/2002 | Johnson et al. | |
| 2002/0143286 A1 | 10/2002 | Tumey | |
| 2002/0161346 A1 | 10/2002 | Lockwood et al. | |
| 2003/0050594 A1 | 3/2003 | Zamierowski | |
| 2003/0108587 A1 | 6/2003 | Orgill et al. | |
| 2004/0039415 A1 | 2/2004 | Zamierowski | |
| 2007/0265585 A1 * | 11/2007 | Joshi et al. | 604/313 |
| 2008/0108977 A1 * | 5/2008 | Heaton et al. | 604/543 |

FOREIGN PATENT DOCUMENTS

| | | |
|---|---|---|
| DE | 847475 | 6/1952 |
| DE | 2809828 | 9/1978 |
| DE | 41 11 122 A1 | 4/1993 |
| EP | 0 620 720 B1 | 3/1998 |
| EP | 0 688 189 B1 | 9/2000 |
| GB | 641061 | 8/1950 |
| GB | 1273342 | 5/1972 |
| GB | 2125296 A | 3/1984 |
| GB | 2380255 A | 4/2003 |
| JP | 1005548 A2 | 1/1989 |
| WO | WO90/11795 | 10/1990 |
| WO | WO91/00718 | 1/1991 |
| WO | WO91/16030 | 10/1991 |
| WO | WO92/19313 | 11/1992 |
| WO | WO92/20299 | 11/1992 |
| WO | WO93/09736 | 5/1993 |
| WO | WO94/20041 | 9/1994 |
| WO | WO96/05873 | 2/1996 |
| WO | WO00/32247 | 6/2000 |

OTHER PUBLICATIONS

Clark, R.A.F., et al., The Molecular and Cellular Biology of Wound Repair, Chapter 1 (1988) (33 pages), Plenum Press, New York.

Mulder, G.D., et al. Clinician's Pocket Guide to Chronic Wound Repair, 1991, pp. 54-55, Wound Healing Publications, Spartanburg, SC.

Chariker, M.E. et al., "Effective Management of Incisional and Cutaneous Fistulae with Closed Suction Wound Drainage," Contemporary Surgery, Jun. 1989, pp. 59-63, vol. 34.

Jeter, K.F. et al. "Managing Draining Wounds and Fistulae: New and Established Methods," Chronic Wound Care: Health Management Publications, 1990, pp. 240-246.

"What's So Special About the Moblvac II Portable Suction System?", Aeros, (1 page).

"Care-E-Vac", Aeros, Aug. 1993 (2 pages).

"Emerson Post-Operative Suction Pumps", Emerson, Series 55. J.H. Emerson Co., Cambridge, MA, (1 page).

"Emerson Transport Suction Unit", Emerson, J.H. Emerson Co., Cambridge, MA, (1 page).

"Instavac Aspirator", Aeros, Aeros Instruments, Inc., Northbrook, IL Oct. 1988, Part No. 1504-02 7M. (1 page).

"Pleur-evac. Adult-Pediatric, Non-Metered." Code No. A-4000. Control No. F7961J (5 pages).

"TUGS (Transportable Universal Gradient Suction", Instruction Manual, Creative Medical Laboratories, Inc., Rochester, Minn. (7 pages).

"Pleur-evac", Deknatel, Div. of Howmedica, Inc. Queens Village, NY (1 page).

"Power Source Multi-Purpose Surgical Aspirator" Sparta Instrument Corp., Hayward, CA (1 page).

"Point 5 Aspirator", Wells Johnson Company, Tucson, AZ (2 pages).

"Wound-Evac ET Closed Wound Suction System", Microtek Heritage, Columbus, MS, No. 0012 (4 pages).

Fleischmann, W., Wund Forum Spezial. IHW '94. "Vakuumversiegelung zur Behandlung von Problemwunden" (with English translation: Vacuum Sealing for Treatment of Problematical Wounds) (7 pages).

Fleischmann, W., "Treatment of Bone and Soft Tissue Defects in Infected Nonunion", Acta Orthopaedica Belgica Suppl. I-1992, vol. 58 (9 pages).

Fleischmann, W., "Vakuumversiegelung zur Behandlung des Weichteilschadens bei offenen Frakturen." (English abstract, no English translation) (5 pages) Unfall Chirurg. Springer-Varlag 1993.

Valenta, A., "Using the Vacuum Dressing Alternative for Difficult Wounds", American Journal of Nursing, Apr. 1994 (2 pages).

Letsou et al. "Stimulation of Adenylate Cyclase Activity in Cultured Endothelial Cells Subjected to Cyclic Stretch." J Cardiovascular Surgery 31. Toronto. Sep. 1990 (pp. 634-639).

Bucalo et al. "Inhibition of Cell Proliferation by Chronic Wound Fluid." Wound Repair and Regeneration. Jul.-Sep. 1993 (pp. 181-186).

Falanga, Vincent. "Growth Factors and Chronic Wounds: The Need to Understand the Microenvironment." Journal of Dermatology, vol. 19, 1992 (pp. 667-672).

Urschel et al. "The Effect of Mechanical Stress on Soft and Hard Tissue Repair; a Review." British Journal of Plastic Surgery, 1988 vol. 41 (pp. 182-186).

Gogia, Prem P. "The Biology of Wound Healing." Ostomy/Wound Management. Nov.-Dec. 1992. pp. 12-20.

Olenius et al., "Mitotic Activity in Expanded Human Skin." Plastic and Reconstructive Surgery. Feb. 1993, pp. 213-215, vol. 91, No. 2.

Rastgeldi, S., "I. Pressure Treatment of Peripheral Vascular Diseases. II. Intermittent Pressure Treatment of Peripheral Vascular Diseases.", Opuscula Medica, Suppl. XXVII, 1972 (49 pages).

Author Unknown., "Hyperemia by Suction Apparatus", Chapter VIII, pp. 74-85.

Saunders, J.W., "Negative-Pressure Device for Controlled Hypotension During Surgical Operations", The Lancet, Jun. 28, 1952, pp. 1286-1287.

Landis et al., "The Effects of Alternate Suction and Pressure on Blood Flow to the Lower Extremities," Robinette Foundation of the Hospital of the University of Pennsylvania, (pp. 925-961).

Hargens et al., "Control of Circulatory Functions in Altered Gravitational Fields" Space Physiology Laboratory, Life Science Division, NASA, Ames Research Center (4 pages).

Wolthuis et al., "Physiological Effects of Locally Applied Reduced Pressure in Man", Physiological Reviews, Jul. 1974, 54:566-595.

Viljanto et al., "Local hyperalimentation of open wounds", BR J Surg., 1976, 63:427-430.

Dillon, "Treatment of Resistant Venous Stasis Ulcers and Dermatitis with the End-Diastolic Pneumatic Compression Boot", Angiology—The Journal of Vascular Diseases, Jan. 1986, pp. 47-55.

Lundvall et al., "Transmission of externally applied negative pressure to the underlying tissue. A study on the upper arm of man", Acta Physiol Scand, 136: 403-409, accepted Jan. 28, 1989.

Klemp et al., "Subcutaneous Blood Flow in Early Male Pattern Baldness", The Journal of Investigative Dermatology, 1989, pp. 725-726.

A. Harle, "Schwachstellen herkommlicher Drainagen", Z. Orthop., 1989, 127: 513-517.

Dunlop et al., "Vacuum drainage of groin wounds after vascular surgery: a controlled trial", Br. J. Surg., 1990, 77: 562-563.

Maddin et al., "The Biological Effects of a Pulsed Electrostatic Field with Specific Reference to Hair: Electrotrichogenesis", International Journal of Dermatology, 1990, 29: 446-450.

Nakayama et al., "A New Dressing Method for Free Skin Grafting in Hands", Ann. Plast. Surg., 1991, 26: 499-502.

Hargens et al., "Lower Body Negative Pressure to Provide Load Bearing in Space", Aviation, Space and Environmental Medicine, Oct. 1991, pp. 934-937.

Author Unknown, "The Not-So-Bald-Truth", Science, Sep. 1992, p. 42 (1 page).

"HiBlow Air Pump", Techno Takatsuki Co., Ltd., Osaka, Japan (1 page).

"Wells Johnson Suction Tips", American Journal of Nursing, Apr. 1994 (1 page).

"Miscellaneous Equipment" IEN Industrial Equipment News, Skokie, IL, (1 page).

Wysocki et al., "Wound Fluid from Chronic Leg Ulcers Contains Elevated Levels of Metalloproteinases MMP-2 and MMP-9." The Society for Investigative Dermatology, Inc., Jul. 1993 (pp. 64-68).

Finley, John M., M.D., "Subclavian Intravenous Catheters", Manual of Wound Dressings, pp. 124-148.

Fleck, et al., "When Negative is Positive: A Review of Negative Pressure Wound Therapy," For submission to the Mar./Apr. 2004 ECPN Wound Care Column (12 pages).

Philbeck Jr., et al., "The Clinical and Cost Effectiveness of Externally Applied Negative Pressure Wound Therapy in the Treatment of Wounds in Home Healthcare Medicare Patients", Ostomy/Wound Management, Jan. 1999; 45(11):41-50.

Murphy et al., "Options in Practice: Care of an Obese Patient with a Pressure Ulcer," 2001, JWOCN, 28:171-6.

Morykwas,, Michael et al., "Vacuum-Assisted Closure: A New Method for Wound Control and Treatment: Animal Studies and Basic Foundation," Annals of Plastic Surgery, Jun. 1997, vol. 38, No. 6 (pp. 553-562).

Mendez-Eastman, Susan, "Negative Pressure Wound Therapy," Plastic Surgical Nursing, Spring 1988, vol. 18, No. 1, (pp. 27-29, 33-37).

Schneider, Andrew, et al., "A New and Reliable Method of Securing Skin Grafts to the Difficult Recipient Bed," Plastic and Reconstructive Surgery, Sep. 1998, vol. 102, No. 4 (pp. 1195-1198).

Rohrich, Rod J. et al., "An Algorithm for Abdominal Wall Reconstruction," Plastic and Reconstructive Surgery, Jan. 2000, vol. 105, No. 1 (pp. 202-216).

Obdeijn, Miryam C. et al., "Vacuum-Assisted Closure in the Treatment of Poststernotomy Mediastinitis," Ann. Thoracic Surgery, 1999; 68:2358-60.

Morykwas, Michael J. et al., "Nonsurgical Modalities to Enhance Healing and Care of Soft Tissue Wounds," Journal of the Southern Orthopedic Association, Winter 1997, vol. 6, No. 4, (pp. 279-288).

Meara, John G. et al., "Vacuum-Assisted Closure in the Treatment of Degloving Injuries," Annals of Plastic Surgery, Jun. 1999, vol. 42, No. 6 (pp. 589-594).

Molnar ,Joseph A. et al., "Single-Stage Approach to Skin Grafting the Exposed Skull," Plastic and Reconstructive Surgery, Jan. 2000, vol. 105, No. 1 (pp. 174-177).

Joseph, Emmanuella et al, "A Prospective Randomized Trial of Vacuum-Assisted Closure Versus Standard Therapy of Chronic Nonhealing Wounds," Wounds 2000; 12(3):60-67.

Greer, Steven E. et al., "Techniques for Applying Subatmospheric Pressure Dressing to Wounds in Difficult Regions of Anatomy," JWOCN, Sep. 1999, vol. 26, No. 5, (pp. 250-253).

ConstaVac™ Closed Wound Drainage System, Stryker Instruments (2 pages).

Obdeijn, Miryam C., et al., "Vacuum-Assisted Closure in the Treatment of Poststernotomy Mediastinitis," Ann. Thoracic Surgery, 1999, 68:2358-60.

Serry, Cyrus, et al., "Sternal Wound Complications: Management and Results," J Thorac Cardiovasc Surg, 1980, 80:861-867.

Tang, A.T.M., et al., "Vacuum-Assisted Closure to Treat Deep Sternal Wound Infection Following Cardiac Surgery," Journal of Wound Care, May 2000, vol. 9, No. 5 (3 pages).

Argenta, Louis C. et al., "Vacuum-Assisted Closure: A New Method for Wound Control and Treatment: Clinical Experience," Annals of Plastic Surgery, Jun. 1997, vol. 38, No. 6 (15 pages).

Putney, F. Johnson, M.D., "The Use of Continuous Negative Pressure After Laryngectomy and Radical Neck Dissection," Surgery, Jul. to Dec. 1956, vol. 103 (5 pages).

Fay, Margaret F., "Drainage Systems—Their Role in Wound Healing," Aorn Journal, Sep. 1987, vol. 46, No. 3 (10 pages).

Fox, James W. et al. "The Use of Drains in Subcutaneous Surgical Procedures," The American Journal of Surgery, Nov. 1976, vol. 132 (3 pages).

Sames, C. Patrick, "Sealing of Wounds With Vacuum Drainage" (1 page).

Davis, T. P., "The Advantages of Suction Drainage in Surgical Wounds," The Medical Journal of Australia, Feb. 1, 1958 (3 pages).

Hartz, Renee S. et al., "Healing of the Perineal Wound," Arch Surg. Apr. 1980, vol. 115 (5 pages).

Morris, A. M., "A Controlled Trial of Closed Wound Suction, Drainage in Radical Mastectomy," The British Journal of Surgery, Jan. 1973 to Dec. 1973, vol. 60 (4 pages).

Berman, Arnold T., et al., "Comparison Between Intermittent (Spring-Loaded) and Continuous Closed Suction Drainage of Orthopedic Wounds: A Controlled Clinical Trial," Orthopedics, Mar. 1990 vol. 13/No. 3 (8 pages).

McFarlane, R. M., "The Use of Continuous Suction Under Skin Flaps," British Journal of Plastic Surgery, 1958-59, vol. XI (12 pages).

Sutton, Warren T. et al., "Suction for Postoperative Wounds," Archives of Surgery, Jan. through Jun. 1961, vol. 82 (8 pages).

Lesser, Arthur J., "The Place of Wound Drainage in Surgery with Description of a New Drain," Archives of Surgery, Dec. 1960, vol. 81, No. 6 (9 pages).

Sheppard, M. D. et al., "Sealed Drainage of Wounds," The Lancet, Jan.-Jun. 1952, vol. One (5 pages).

Ramirez, Oscar M. et al., "Optimal Wound Healing Under Op-Site Dressing," Plastic and Reconstructive Surgery, Mar. 1984, vol. 73, No. 3 (3 pages).

Silvis, Richard S. et al., "The Use of Continuous Suction Negative Pressure Instead of Pressure Dressing," Annals of Surgery, Jul.-Dec. 1955, vol. 142 (7 pages).

Giovannini, Uberto M., et al., "Interest of Negative Pressure Therapy in the Treatment of Postoperative Sepsis in Cardiovascular Surgery," Wounds, 2001, Health Management Publications, 13(2):82-87. (7 pages).

Kostiuchenok, B. M., et al., "The Vacuum Effect in the Surgical Treatment of Purulent Wounds," Russian Journal, Vestnik Khirurgii, Sep. 1986 (pp. 18-21).

Davydov, Yu A., et al., "Vacuum Therapy in the Treatment of Purulent Lactation Mastitis," Russian Journal, Vestnik Khirurgii, Sep. 1986 (pp. 66-70).

Usupov, Y. N. et al., "Active Wound Drainage," Russian Journal, Vestnik Khirurgii, Apr. 1987 (pp. 42-45).

Davydov, Yu A., et al., "The Bacteriological and Cytological Assessment of Vacuum Therapy of Purulent Wounds," Russian Journal, Vestnik Khirurgii, Oct. 1988, (pp. 48-52).

Davydov, Yu A., et al., "Concepts for Clinical Biological Management of the Wound Process in the Treatment of Purulent Wounds Using Vacuum Therapy," Russian Journal, Vestnik Khirurgii, Feb. 1991 (pp. 132-135).

Davydov IA., et al., "Vacuum therapy of acute supportive diseases of soft tissues and suppurative wounds," Vestnik Khirurgii Imeni i-i-Grekova. Sep. 1988, 141(9):43-6 (Abstract—1 page).

Tadych K., et al., "Postmastectomy seromas and wound drainage," Surgery, Gynecology & Obstetrics, Dec. 1876, 165(6):483-7 (Abstract—1 page).

Iusupov IN, et al., "Active drainage of a wound," Vestnik Khirurgii Imeni i-i-Grekova. Apr. 1987, 138(4):42-6 (Abstract—1 page).

Hendrich V. et al., "Suction-drainage in the treatment of chronic osteomyelitis," Unfallchirurgie. Apr. 1986, 12(2):101-3 (Abstract—1 page).

Harle A., "Postoperative wound suction drainage and its effect on wound healing," Zeitschrift fur Orthopadie und Ihre Grenzgebiete. May-Jun. 1985, 123(3):395-402 (Abstract—1 page).

Smith Sr., et al., "Surgical drainage," British Journal of Hospital Medicine, Jun. 1985, 33(6):308, 311, 314-15 (Abstract—1 page).

Lokhvitski SV. Bil'Kevich AA., "[Treatment of carbuncles]," Vestnik Khirurgii Imeni i-i-Grekova, Jan. 1984, 132(1):71-4 (Abstract—1 page).

Harle A., "Weakness of conventional drainage systems," Zeitschrift fur Orthopadie und Ihre Grenzgebiete, Jul.-Aug. 1989, 127(4):513-7 (Abstract—1 page).

Durandy Y., et al., "Mediastinal infection after cardiac operation. A simple closed technique." Journal of Thoracic & Cardiovascular Surgery, Feb. 1989, 97(2):282-5 (Abstract—1 page).

Healy DA., et al., "Prophylactic closed suction drainage of femoral wounds in patients undergoing vascular reconstruction." Journal of Vascular Surgery, Aug. 1989, 10(2):166-8 (Abstract—1 page).

Gerngross H., et al., "Gravity drainage versus suction drainage: an experimental and clinical study." Unfallchirurg. Jan. 1989, 92(1):37-42 (Abstract—1 page).

Draca, P., et al., "Extraperitoneal transabdominal vacuum drainage of the parametrial cavity and suprapubic drainage of the urinary bladder after radical hysterectomy." Jugoslavenska Ginekologija i Perinatologija, May-Aug. 1989, 29(3-4):129-32 (Abstract—1 page).

Willett KM., et al., "The effect of suction drains after total hip replacement." Journal of Bone & Joint Surgery, Aug. 1988, British vol. 70 (4):607-10 (Abstract—1 page).

Tittel K., et al., "VariDyne—new standards in postoperative wound drainage." Unfallchirurgie. Apr. 1988, 14(2):104-7 (Abstract—1 page).

Davydov IA., et al., "Vacuum therapy of actute suppurative diseases of soft tissues and suppurative wounds." Vestnik Khirurgii Imeni i-i-Grekova., Sep. 1988, 141(9):43-6 (Abstract—1 page).

Tadych K., et al., "Postmastectomy seromas and wound drainage." Surgery, Gynecology & Obstetrics, Dec. 1987, 165(6):483-7 (Abstract—1 page).

Moss AL., "The DIY mini suction drain." British Journal of Plastic Surgery, Sep. 1987, 40(5):542-3 (Abstract—1 page).

Iusupov IN, et al., "Active drainage of a wound." Vestnik Khirurgii Imeni i-i-Grekova. Apr. 1987, 138(4):42-6 (Abstract—1 page).

Orr JW., et al., "Closed suction pelvic drainage after radical pelvic surgical procedures." American Journal of Obstetrics & Gynecology, Oct. 1986, 155(4):867-71 (Abstract—1 page).

Svedman P., et al., "A dressing system providing fluid supply and suction drainage used for continous or intermittent irrigation." Annals of Plastic Surgery, Aug. 1986, 17(2):125-33 (Abstract—1 page).

Nasser NA., "The use of the Mini-Flap wound suction drain in maxillofacial surgery." Annals of the Royal College of Surgeons of England., May 1986, 68(3):151-3 (Abstract—1 page).

Hendrich V., et al., "Suction-drainage in the treatment of chronic osteomyelitis." Unfallchirurgie, Apr. 1986, 12(2):101-3 (Abstract—1 page).

Diament MJ., et al., "Percutaneous aspiration and catheter drainage of abscesses." Journal of Pediatrics, Feb. 1986, 108(2):204-8 (Abstract—1 page).

Chinn SD, et al., "Closed wound suction drainage." Journal of Foot Surgery, Jan.-Feb. 1985, 24(1):76-81 (Abstract—1 page).

Harle A., "Postoperative wound suction drainage and its effect on wound healing." Zeitschrift fur Orthopadie and Ihre Grenzgebiete, May.-Jun. 1985, 123(3):395-402 (Abstract—page).

Pruett TL., et al., Percutaneous aspiration and drainage for suspected abdominal infection. Surgery, Oct. 1984, 96(4):731-7 (Abstract—1 page).

Smith Sr., et al., "Surgical drainage." British Journal of Hospital Medicine, Jun. 1985, 33(6):308, 311, 314-15 (Abstract—1 page).

Kawashima M., et al., "A new instrument for closed irrigation-suction treatment." Nippon Seikeigeka Gakkai Zasshi—Journal of the Japanese Orthopedic Association, Jun. 1983, 57(6):643-50, (Abstract—1 page).

Vergeret J., et al., "Endocavitary drainage (Monaldi's technic) in the treatment of pulmonary abscess." Revue Francaise des Maladies Respiratoires, 1983, 11(3):201-7 (Abstract—1 page).

Vatanasapt V., et al., "Red rubber bulb, cheap and effective vacuum drainage." Journal of the Medical Association of Thailand, Apr. 1989, 72(4):193-7 (Abstract—1 page).

Rudberg C., et al., "How does the increasing filling of the vacuum source diminish the suction in modern portable drainage systems?" Acta Chirurgica Scandinavica, Jan. 1988, 154(1):1-8 (Abstract—1 page).

Cooper AJ., "Preliminary experience with a vacuum constriction device (VCD) as a treatment for impotence." Journal of Psychosomatic Research, 1987, 31(3):413-8 (Abstract—1 page).

Hedges Jr., et al., "Evaluation of venous distension device: potential aid for intravenous cannulation." Annals of Emergency Medicine, May 1986, 15(5):540-3 (Abstract—1 page).

Ramirez OM., et al., "Optimal wound healing under Op-Site dressing." Plastic & Reconstructive Surgery, Mar. 1984, 73(3):474-5 (Abstract—1 page).

Hollender L.F., et al., "Suction drainage in general and digestive surgery. Apropos of the use of Reliavac material." Journal de Chirurgie, Aug.-Sep. 1984, 121(8-9):539-40 (Abstract—1 page).

Nakayama Y, et al., "A new dressing method for free skin grafting in hands." Ann Plast Surg 1991 May;26(5):499-502. (Abstract—1 page).

Fay MF., "Drainage systems. Their role in wound healing." AORN J Sep. 1987;46(3):442-55. (Abstract—1 page).

Durandy Y, et al., "Mediastinal infection after cardiac operation. A simple closed technique." J Thorac Cardiovasc Surg, Feb. 1989, 97(2):282-5. (Abstract—1 page).

Berger DL., "Use of drains in foot surgery." J Foot Surg., May-Jun. 1988; 27(3):245-7. (Abstract—1 page).

Insupov Iun, et al., "Active drainage of a wound." Vestn Khir Im I I Grek, Apr. 1987, 138(4):42-6. (Abstract—1 page).

Fox JW $4^{TH,}$, et al., "The use of drains in subcutaneous surgical procedures." Am J Surg., Nov. 1976, 132(5):673-4. (Abstract—1 page).

Bourke JB, et al., "A comparison between suction and corrugated drainage after simple mastectomy: a report of a controlled trial." Br J Surg., Jan. 1976, 631(1):67-9. (Abstract—1 page).

Chinn SD, et al., "Closed wound suction drainage." J Foot Surg., Jan.-Feb. 1985, 24(1):76-81. (Abstract—1 page).

Guharay BN, et al., "The pacemaker-twiddler's syndrome: another disadvantage of abdominal implantation of pulse generators." Br J Surg., Sep. 1977, 64(9):655-60. (Abstract—1 page).

Elliot MS, et al., "Management of the perineal wound with constant irrigation and suction after abdominoperineal excision for cancer of the rectum. A new suction/irrigation drain." S Afr Med J., Nov. 10, 1979, 56(20):796-98. (Abstract—1 page).

Brummelkamp WH, et al. "Primary closure of the perineum and vacuum drainage after abdominoperineal excision.", Acta Chir Belg., Sep.-Oct. 1983, 83(5)358-64 (Abstract—1 page).

Garcia-Rinaldi R., et al., "Improving the Efficiency of Wound Drainage Catheters.", Am J Surg Sep. 1975, 130(3):372-3 (Abstract—1 page).

McCormack T.T., et al., "Abdominal drainage following cholecystectomy: high, low, or no suction?", Ann R Coll Surg., England, Sep. 1983, 65(5):326-8 (Abstract—1 page).

Saha SK, et al., "A Study of Perineal Wound Healing After Abdominoperineal Resection.", Br J Surg., Jul. 1976, 63(7):555-8 (Abstract—1 page).

Werner, H.P., "Complications and Risks of Suction Drainage.", Z Gesamte Hyg,, Feb. 1990, 36(2):94-9 (Abstract—1 page).

Azad, S. et al., "Topical Negative Pressure May Help Chronic Wound Healing", BMJ May 4, 2002; 324:1100 (2 pages).

Author Unknown, "Three Techniques to Save the Lives of Children with Burns, to Close Wounds and Restore Walking Ability.", British Association of Plastic Surgeons, Press Release—Dec. 1996 (3 pages).

Chariker-Jeter® Wound Drainge Kit, Blue Medical, La Costa, California (1 page).

Wooding-Scott® Drainage/Irrigation Kit, Blue Sky Medical, La Costa, California (1 page).

Rosser, Charles, et al., "A New Technique to Manage Perineal Wounds", Infections in Urology, Mar./Apr. 2000 (4 pages).

The V.A.C. Vacuum Assisted Closure, The V.A.C. System, KCI, San Antonio, Texas (4 pages).

V.A.C. Recommended Guidelines for Use, Physician and Caregiver Reference Manual, KCI, San Antonio, Texas (20 pages).

MiniV.A.C.™ Vacuum Assisted Closure Summary Sheet, KCI, San Antonio, Texas (4 pages) © 2000, 2001.

The V.A.C® System, The Truth About Misuse . . . , KCI, San Antonio, Texas, Oct. 2000 (2 pages).

V.A.C.® Operations Summary, May 2001, KCI, San Antonio, Texas (2 pages).

V.A.C.® Soft Foam, KCI, San Antonio, Texas, Aug. 2001 (4 pages).

The V.A.C. Patient and Family Handbook, KCI, San Antonio, Texas (21 pages).

Excerpts from Articles Published on the V.A.C.® Device, 2001, KCI, San Antonio, Texas (1 page).

Mendez Eastman, Susan, "When Wounds Won't Heal", RN, Jan. 1998 (pp. 1-8).

"Wound VAC good for some home health patients, but costly for others,", www.myhomehealth.com, Mar. 29, 2002 (3 pages).

Argenta, Louis C. et al., "V.A.C.® Wound Closure Device Case Study #1.", KCI Therapeutic Services, Inc., San Antonio, Texas Apr. 1998 (1 page).

Argenta, Louis C. et al., "The V.A.C.® Case Study #2", 1995 Kinetic Concepts, Inc. (1 page).

Argenta, Louis C. et al., "V.A.C.® Wound Closure Device Case Study #3", KCI Therapeutic Services, Inc., San Antonio, Texas, Apr. 1998 (1 page).

Argenta, Louis C. et al., "The V.A.C.® Case Study #4", 1995 Kinetic Concepts, Inc. (1 page).

Argenta, Louis C. et al., "V.A.C.® Wound Closure Device Case Study #5", KCI Therapeutic Services, Inc., San Antonio, Texas, Apr. 1998 (1 page).

"V.A.C.® Wound Closure Device Case Study #6", KCI Therapeutic Services, Inc., San Antonio, Texas, Apr. 1998 (2 pages).

"The V.A.C.® Case Study #7", KCI Therapeutic Services, Inc., San Antonio, Texas, Jun. 1996 (2 pages).

"V.A.C.® Wound Closure Device Case Study #8", KCI Therapeutic Services, Inc., San Antonio, Texas, Apr. 1998 (2 pages).

"The V.A.C.® Case Study #10", Kinetic Concepts, Inc., © 1996 (2 pages).

"V.A.C.® Wound Closure Device Case Study #11", KCI Therapeutic Services, Inc., San Antonio, Texas, Apr. 1998 (2 pages).

Harkiss, K. J., "Surgical Dressings and Wound Healing", 1971 Bradford University Press and Crosby Lockwood & Son Ltd., (13 pages).

* cited by examiner

FLAT-HOSE ASSEMBLY FOR WOUND DRAINAGE SYSTEM

FIELD OF INVENTION

The invention relates to systems for treating wounds by the application of negative pressure and to devices for use in such systems.

BACKGROUND OF THE INVENTION

Negative pressure, also referred to as suction, has proven to be a successful technique for the healing of wounds. Negative pressure is applied by a vacuum source through tubing that is attached to a dressing that covers a wound and healthy skin beyond the wound perimeter. Present systems typically use commercially available round tubing made of various materials such as, PVC, nylon, urethane, or similar polymeric materials. One end of the tubing is connected to the vacuum source and a collection device is located between the vacuum source and the wound. A second end of the tubing passes through the dressing in order to evacuate exudates from the wound and place the exudates into the collection device. An airtight seal needs to be maintained between the healthy skin and the dressing as well as between the tubing and the dressing.

Several disadvantages exist with the existing systems. First, it is difficult to make an airtight seal between the dressing and the tubing. If the seal is not airtight, the vacuum will be lost and no exudates will be removed from the wound. Second, the round tubing at the wound site often creates pressure points on the patient as the patient moves around. The round tubing may end up underneath the patient, causing wounds or other patient discomfort. A third disadvantage to the currently available systems is that it is easy to cause the tubing to be bent or kinked, blocking the flow of exudates and inhibiting the application of negative pressure. Thus, a need exists for a hose assembly for a negative pressure wound treatment system that maintains a better seal with a wound dressing, is not as susceptible to blocking the flow through the tubing by kinking, and is less likely to cause patient discomfort or further pressure points.

SUMMARY OF THE INVENTION

According to one embodiment a flat-hose assembly has a proximal end and a distal end adapted for use with a negative pressure wound drainage system. The flat-hose assembly comprises a top layer, a bottom layer, and a filter layer. The bottom layer forms an opening at the distal end of the flat-hose assembly to allow exudates of a wound to flow into the flat-hose assembly. The filter layer is disposed between the top layer and the bottom layer. The top and bottom layer form a seal area along a periphery of the top layer and the bottom layer to seal the filter layer therebetween.

According to another embodiment, a closed wound drainage system comprises a wound dressing, a flat-hose assembly, a collection bag, and a vacuum pump. The wound dressing is adapted to be positioned over a wound area of a patient. The wound dressing forms a first opening over the wound area. The flat-hose assembly has a top layer, a bottom layer, a filter layer, a first hose fitting, and a second hose fitting. The filter layer is positioned between the top layer and the bottom layer. The bottom layer forms a second opening adapted to align with the first opening of the wound dressing. The collection bag is in communication with the flat-hose assembly. The collection bag is adapted to collect material from the wound drawn through the flat-hose assembly. The vacuum pump applies negative pressure to the wound. The vacuum pump is in communication with the collection bag and the flat-hose assembly.

According to a further embodiment, a flat-hose assembly adapted for use with a negative pressure wound drainage system is provided. The flat-hose assembly has a proximal end and a distal end. The flat-hose assembly comprises a top layer, a bottom layer, a filter layer, a first hose fitting, a second hose fitting and an adhesive. The top layer forms a first opening and a second opening therethrough at the proximal end of the top layer. The openings are adapted to apply negative pressure to the flat-hose assembly. The bottom layer forms a third opening at the distal end of the bottom layer. The third opening allows exudates of a wound to flow into the flat-hose assembly. The filter layer is disposed between the top layer and the bottom layer. The filter layer is adapted to prevent contact between the top layer and the bottom layer other than at a periphery of the top layer and the bottom layer. The filter layer is further adapted to trap large particles of exudates from a wound within the flat-hose assembly. The top layer and the bottom layer form a seal area along a periphery of the top layer and the bottom layer that seals the filter layer therebetween. The first hose fitting protrudes through a first opening formed in the distal end of the top layer and is adapted to connect the flat-hose assembly to the negative pressure wound drainage system. The second hose fitting protrudes through a second opening formed in the distal end of the top layer and is adapted to connect the flat-hose assembly to the negative pressure wound drainage system. The adhesive is adapted to connect the flat-hose assembly to a wound dressing of the wound drainage system.

The above summary of the present invention is not intended to represent each embodiment or every aspect of the present invention. The detailed description and Figures will describe many of the embodiments and aspects of the present invention.

BRIEF DESCRIPTION OF THE DRAWINGS

The foregoing and other advantages of the invention will become apparent upon reading the following detailed description and upon reference to the drawings.

Figure 1:
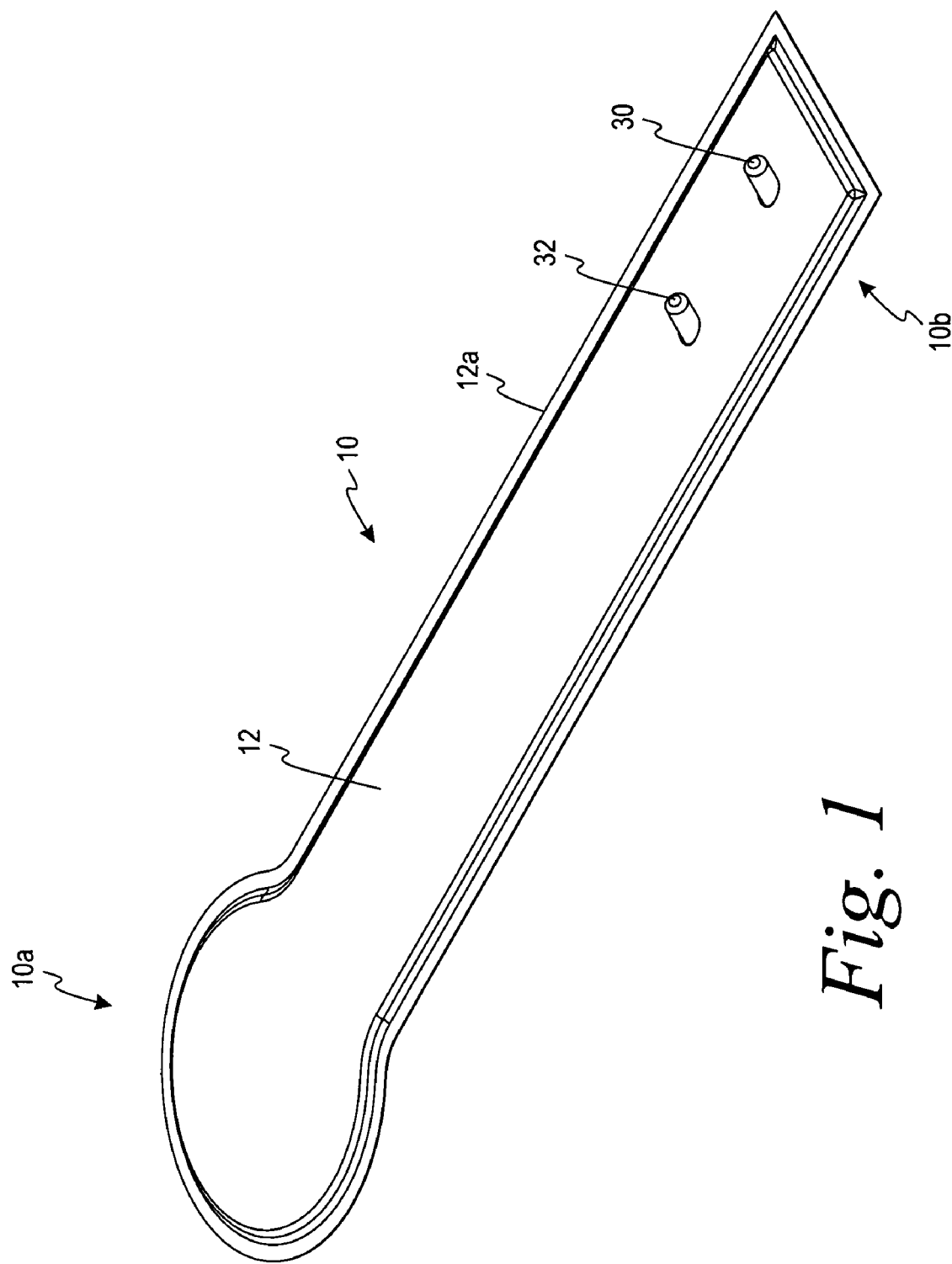
FIG. 1 is a top isometric view of a flat-hose assembly for use in a wound drainage system according to one embodiment.
Figure 2:
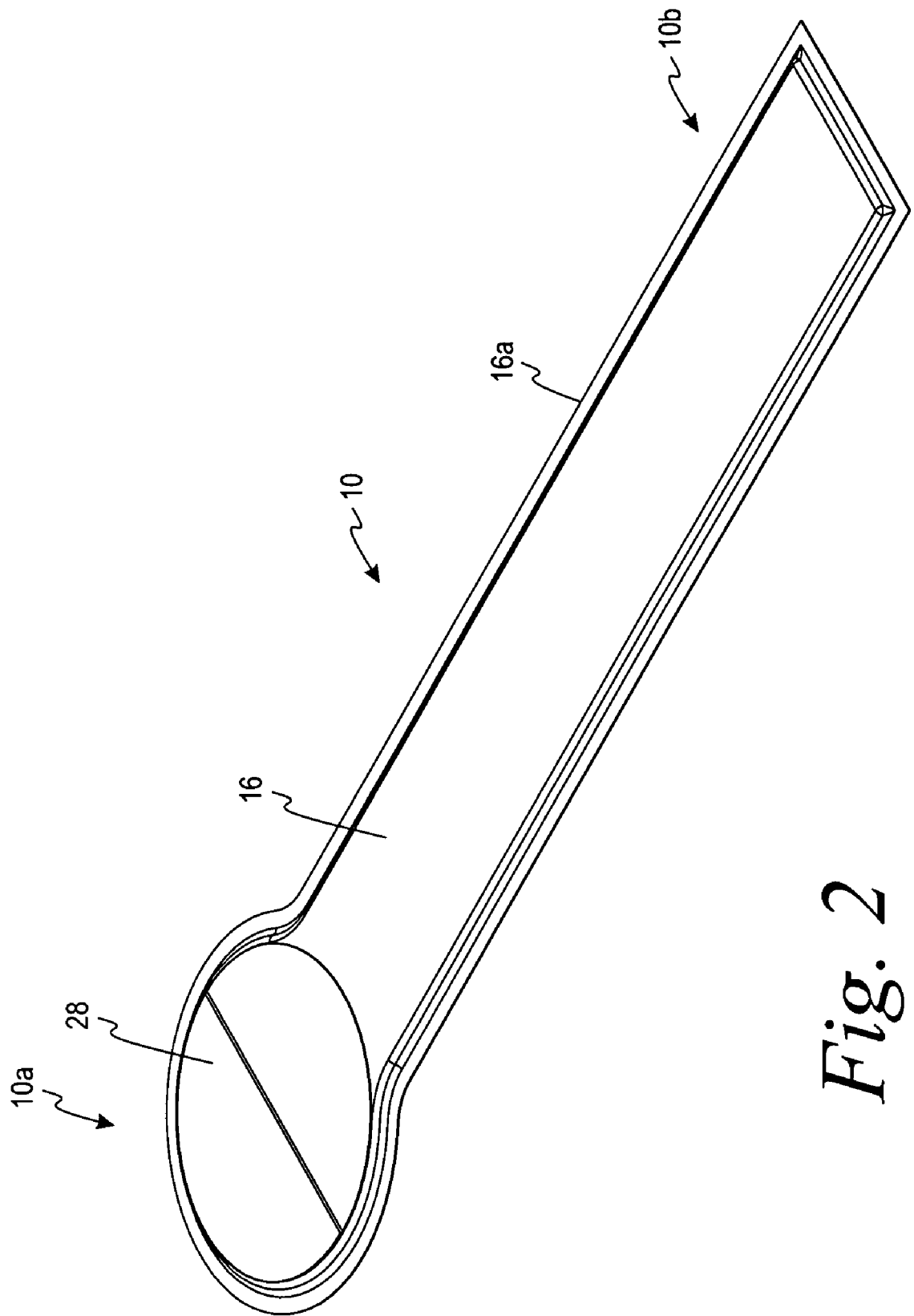
FIG. 2 is a bottom isometric view of the flat-hose assembly of FIG. 1.
Figure 3:
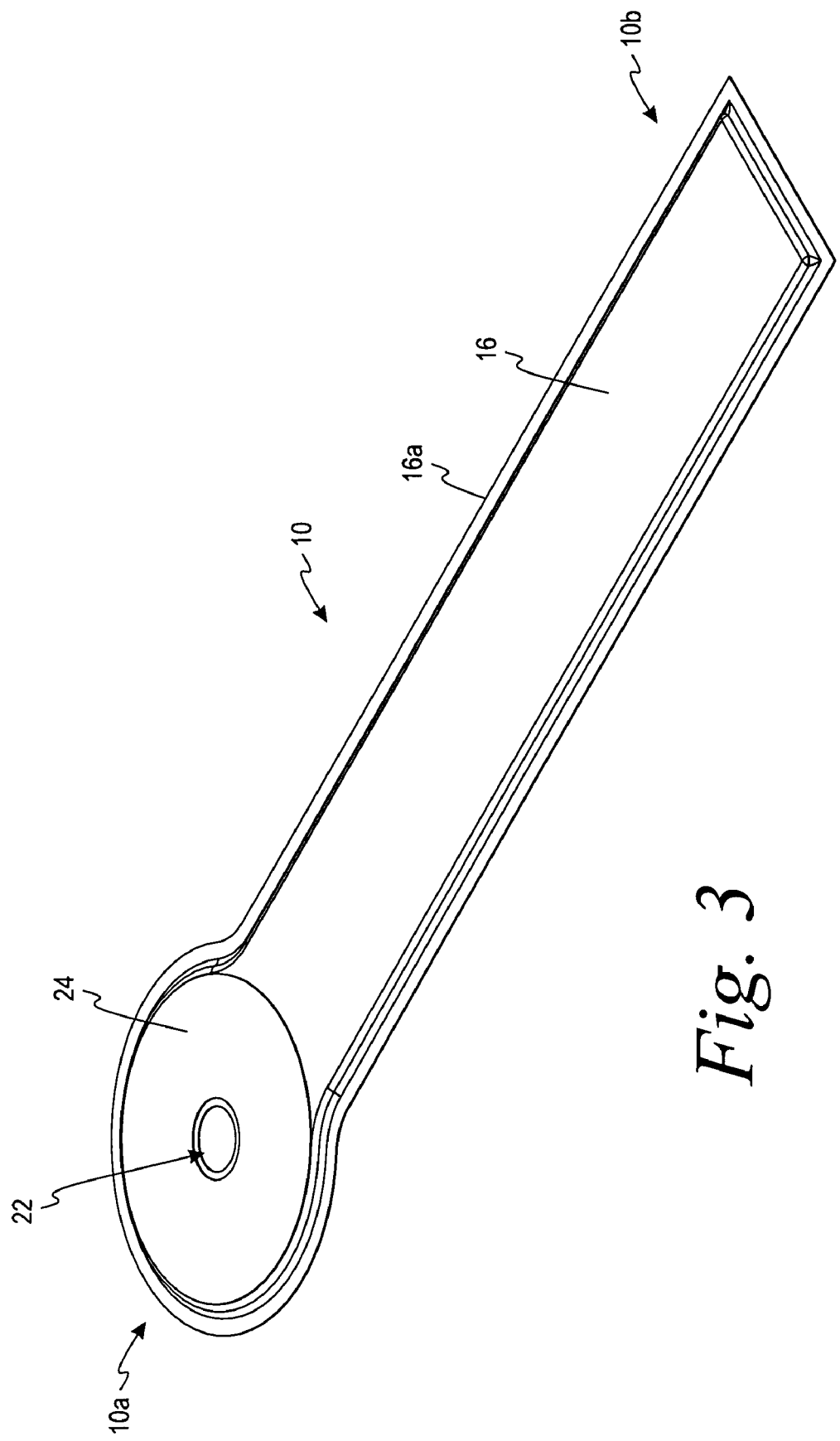
FIG. 3 is a bottom isometric view of the flat-hose assembly of FIG. 1 with a protective backing removed.
Figure 4:
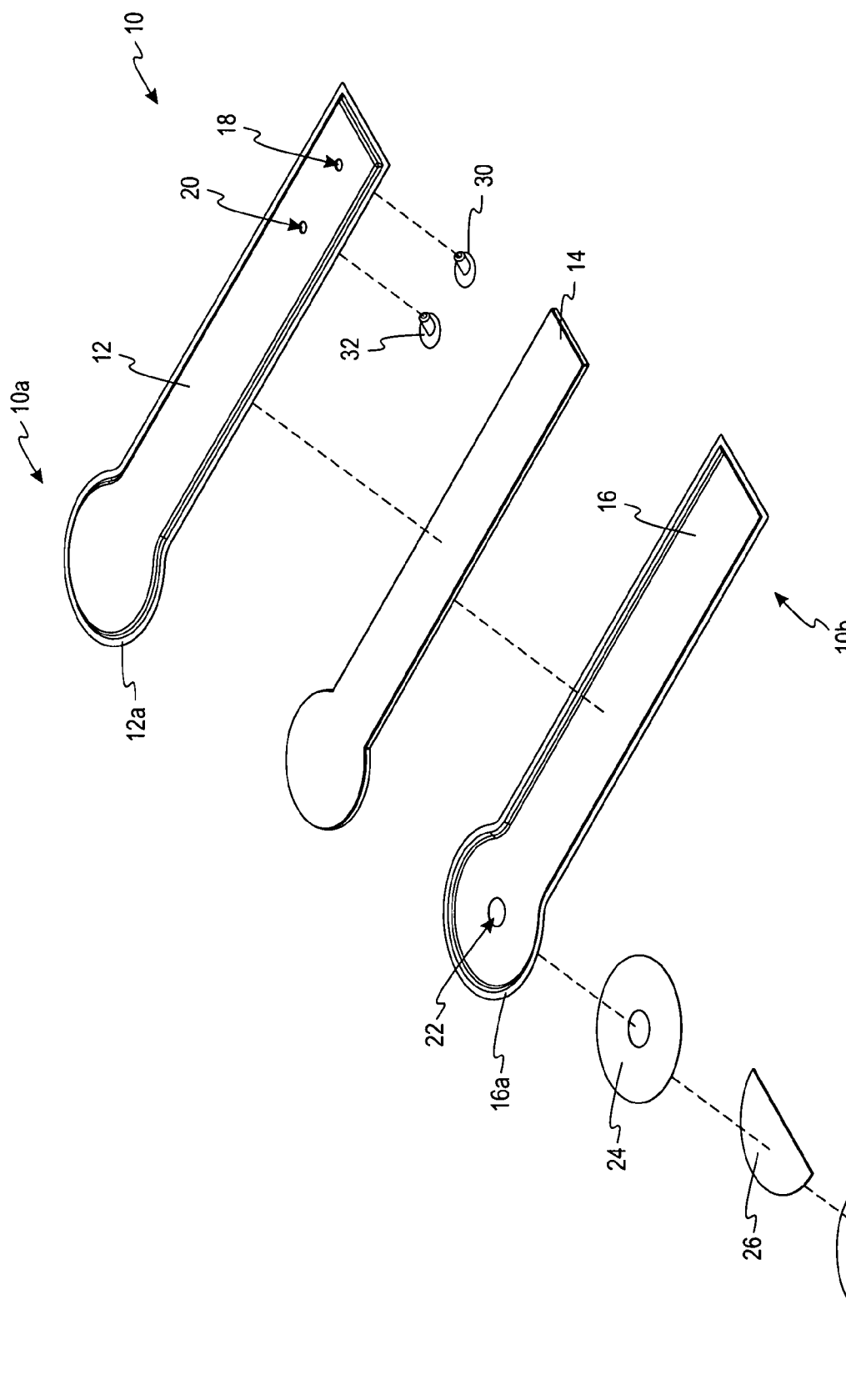
FIG. 4 is an exploded isometric view of the flat-hose assembly of FIG. 1.

While the invention is susceptible to various modifications and alternative forms, specific embodiments thereof have been shown by way of example in the drawings and will herein be described in detail. It should be understood, however, that it is not intended to limit the invention to the particular forms disclosed but, on the contrary, the intention is to cover all modifications, equivalents, and alternatives falling within the spirit and scope of the invention.

DESCRIPTION OF ILLUSTRATIVE EMBODIMENTS

As shown in FIGS. 1-4, a flat-hose assembly 10 for use in a wound drainage system is shown. The flat-hose assembly 10 has a top layer 12, a filter layer 14, and a bottom layer 16. The filter layer 14 is located between the top layer 12 and the bottom layer 16. The top layer 12 and the bottom layer 16 form a seal along a periphery 12a of the top layer 12 and a periphery 16a of the bottom layer 16 such that the filter layer 14 is disposed between the top layer 12 and the bottom layer 16. The filter layer 14 is enclosed within the top layer 12 and the bottom layer 16.

The flat-hose assembly 10 has a distal end 10a and a proximal end 10b. The distal end 10a is generally larger than the proximal end 10b of the flat-hose assembly 10. The distal end 10a is adapted to interact with a wound dressing to allow exudates from a wound to flow into the wound drainage system (see FIG. 5). The distal end 10a The proximal end 10b is adapted to allow exudates to flow away from the wound and wound dressing and enter the wound drainage system. As shown in FIGS. 1-4, the surface area of the distal end 10a of the flat-hose assembly 10 is greater than the surface area of the proximal end 10b of the flat-hose assembly 10. It is contemplated that other embodiments may have a larger distal end than a proximal end. Further, the embodiment shown in FIGS. 1-4 shows the distal end having a circular shape and the proximal end having a rectangular shape. It is contemplated that other shapes may be used. The distal end 10a of the flat-hose assembly 10 is sized to allow a sufficiently sized third opening 22 to draw exudates away from a wound and to allow the flat-hose assembly 10 to form an airtight seal with a wound dress 120 (see FIG. 5).

As shown in FIGS. 1-4, the flat-hose assembly 10 has an overall length of about 12 inches, the distal end 10a has a circular shape with a diameter of about 3.5 inches, while the rectangularly shaped portion of the flat-hose assembly 10 has a width of about 1.75 inches. However, these dimensions may vary based on a patient's wound, the geometry of the wound dressing 120 (see FIG. 5), and the location of the patient's wound on the patient's body.

The top layer 12 forms a first opening 18 and a second opening 20. The first and second openings 18, 20 allow hose fittings 30, 32 to pass through the first layer 12 to connect the flat-hose assembly 10 to a wound drainage system (see FIG. 5) to create a negative pressure within the flat-hose assembly 10.

The bottom layer 16 forms a third opening 22. The third opening 22 aligns and interacts with an opening in a wound dressing (not shown) to allow exudates of the wound to flow into the flat-hose assembly 10 based on the vacuum created by the wound drainage system. The third opening 22 allows the flat-hose assembly to be in communication with the wound when properly aligned with the opening in the wound dressing. It is contemplated that additional opening may be formed in the bottom layer 16. For example, multiple openings may be used in place of a single opening 22 to remove exudates from a wound, openings may be provided to deliver medication to the wound, openings may be provided to flush the wound with saline solution without removing the wound dressing, and/or openings may be provided in the bottom layer 16 to introduce electrical stimuli to the wound.

It is contemplated that a variety of materials may be used to form the top layer 12 and the bottom layer 16. Non-limiting examples of materials suitable for forming the top and bottom layers 12, 16 include polymeric materials such as vinyl, urethane, laminated nylon, non-woven materials, and laminated non-woven materials.

The materials selected to form the top layer 12 and the bottom layer 16 of the flat-hose assembly 10 may be generally transparent, generally translucent, or generally opaque. Generally transparent and generally translucent top and bottom layers 12, 16 allow a healthcare provider to observe the flow and color of the exudates from the wound. Therefore, a healthcare provider may be able to observe changes in the condition of a patient's wound without having to remove the wound treatment.

The seal between the top layer 12 and the bottom layer 16 is generally limited to the periphery 12a and 16a of the respective top layer 12 and the bottom layer 16. The seal between the top layer 12 and the bottom layer 16 may be formed in a variety of manners. It is contemplated that the seal may be formed by an RF weld, an adhesive material, a cohesive material, or any additional known sealing method.

The filter layer 14 acts as a spacer to separate the top layer 12 from the bottom layer 16 when negative pressure is applied to the flat-hose assembly 10, thus preventing the top layer 12 from contacting the bottom layer 16 away from the peripheries 12a, 16a where the seal is formed. The filter layer 14 sufficiently spaces the top layer 12 from the bottom layer 16 by filling most of the area between the top layer 12 and the bottom layer 16 so that exudates may flow between the top layer 12 and the bottom layer 16 allowing the wound to be drained. The filter layer 14 allows exudates to flow due to the porosity of the filter layer material. Additionally, the filter layer 14 may have an absorbent and/or wicking property to help to allow exudates to flow.

The filter layer 14 may also have a filter feature that traps large particles of exudates from the wound to prevent these large particles from entering the wound drainage system (see FIG. 5) and clogging or damaging the wound drainage system. The filter layer 14 may be designed to at least trap particles of exudates larger than an inside diameter of tubing 150, 160 used in a wound care system 100 (FIG. 5), to prevent the tubing 150, 160 from clogging.

One of several materials may be used to form the filter layer 14. Contemplated materials include, but are not limited to, cotton, polymeric fiber, filter screen material, and other known materials. Desirable material for utilization in the filter layer 14 is a material that is porous, flexible, and capable of being made into a generally flat shape. The filter layer 14 material allows a patient to lay on the assembly, and still allow the flat-hose assembly 10 to pass exudates.

The filter layer 14 has diameter of about 2.625 inches at a distal end 10a of the flat-hose assembly 10, while a rectangularly shaped portion of the filter layer 14 has a width of about 1.25 inches. It is contemplated that the size of the filter layer 14 will vary as the size and shape of the flat-hose assembly 10 varies.

Thus, it is contemplated that a filter layer may be used that acts primarily as a spacer to separate the top layer from the bottom layer of a flat-hose assembly.

An adhesive 24 attaches to a bottom surface of the bottom layer 16. The adhesive 24 may be a commercially available double-sided adhesive with peal-away liners, such as those manufactured by 3M® or TESATAPE®. The adhesive 24 is selected form a material to allow the adhesive 24 to form an airtight seal with the wound dressing 110 (see FIG. 5). As the material of the dressing 110 may vary, the material of the adhesive 24 may also vary in order to be compatible with the wound dressing 110.

The adhesive 24 generally has a similar shape to that of the distal end 10a of the flat-hose assembly 10. The adhesive 24 is covered by a first protective backing 26 and a second protective backing 28. The protective backings 26, 28 prevent the adhesive 24 from being exposed prior to the flat-hose assembly 10 being used by a healthcare provider. Generally, the protective backings 26, 28 will be shaped similarly to the distal end 10a of the flat-hose assembly 10 to cover the adhesive 24. When the flat-hose assembly is used, the first and second protective backings 26, 28 are removed, exposing the adhesive 24. The first protective backing 26 contacts the adhesive 24 over approximately a first half the area of the adhesive 24, while the second protective backing covers the contacts the adhesive over approximately a second half of the adhesive 24. A portion of the second protective backing 28 additionally covers the first protective backing 26. Thus, the portion of the second protective backing 28 that covers the first protective backing 26 does not contact the adhesive 24. The portion of the second protective backing 28 not contacting the adhesive 24 allows a healthcare provider to more easily remove the second protective backing 28 by grasping the portion not contacting the adhesive, and pulling the second protective backing 28 off of the flat-hose assembly 10. The healthcare provider may then remove the first protective backing 26 to fully expose the adhesive 24. While two protective backings are shown in FIGS. 1-4, it is contemplated that a single protective backing may be used. It is also contemplated that more than two protective backings may be used.

The adhesive 24 allows the flat-hose assembly 10 to attach to a wound dressing (see FIG. 5) and forms a seal between the flat-hose assembly 10 and the wound dressing. The adhesive 24 is shaped to allow the third opening 22 of the bottom layer 16 of the flat-hose assembly 10 to be in communication with the wound dressing. The adhesive 24 allows the flat-hose assembly 10 to form an airtight seal with a wound dressing.

The flat-hose assembly 10 is generally flexible, i.e. easily deformable, and the flexible nature and the thin shape, generally less than 0.5 inches thick, of the flat-hose assembly 10 reduces the pressure points the flat-hose assembly 10 may cause on a patient.

The flat-hose assembly may be folded, bent, or crimped, and the filter layer 14, along with the overall shape and flexible nature of the flat-hose assembly 10 continues to allow exudates to flow through the flat-hose assembly 10, even when the flat-hose assembly 10 is bent. The fact that exudates and other liquids continue to pass through the flat-hose assembly 10 allows the removal of exudates and other liquids from the wound to continue even after the flat-hose assembly is bent. Exudates continue to flow through the flat-hose assembly 10 because the flexible material used in the flat-hose assembly 10 and the presence of the filter layer 14 prevent the top layer 12 from contacting the bottom layer 16 thus preventing the crimping off of the flat-hose assembly.

The flexible nature of the flat-hose assembly 10 additionally allows the flat-hose assembly 10 to be bent by a healthcare provider such that the flat-hose assembly 10 is positioned relative to a patient in a manner for optimal patient care. The flat-hose assembly 10 may be secured to the patient, such as with tape, after being bent by the healthcare provider, and still allow exudates to flow through the flat-hose assembly 10.

Figure 5:
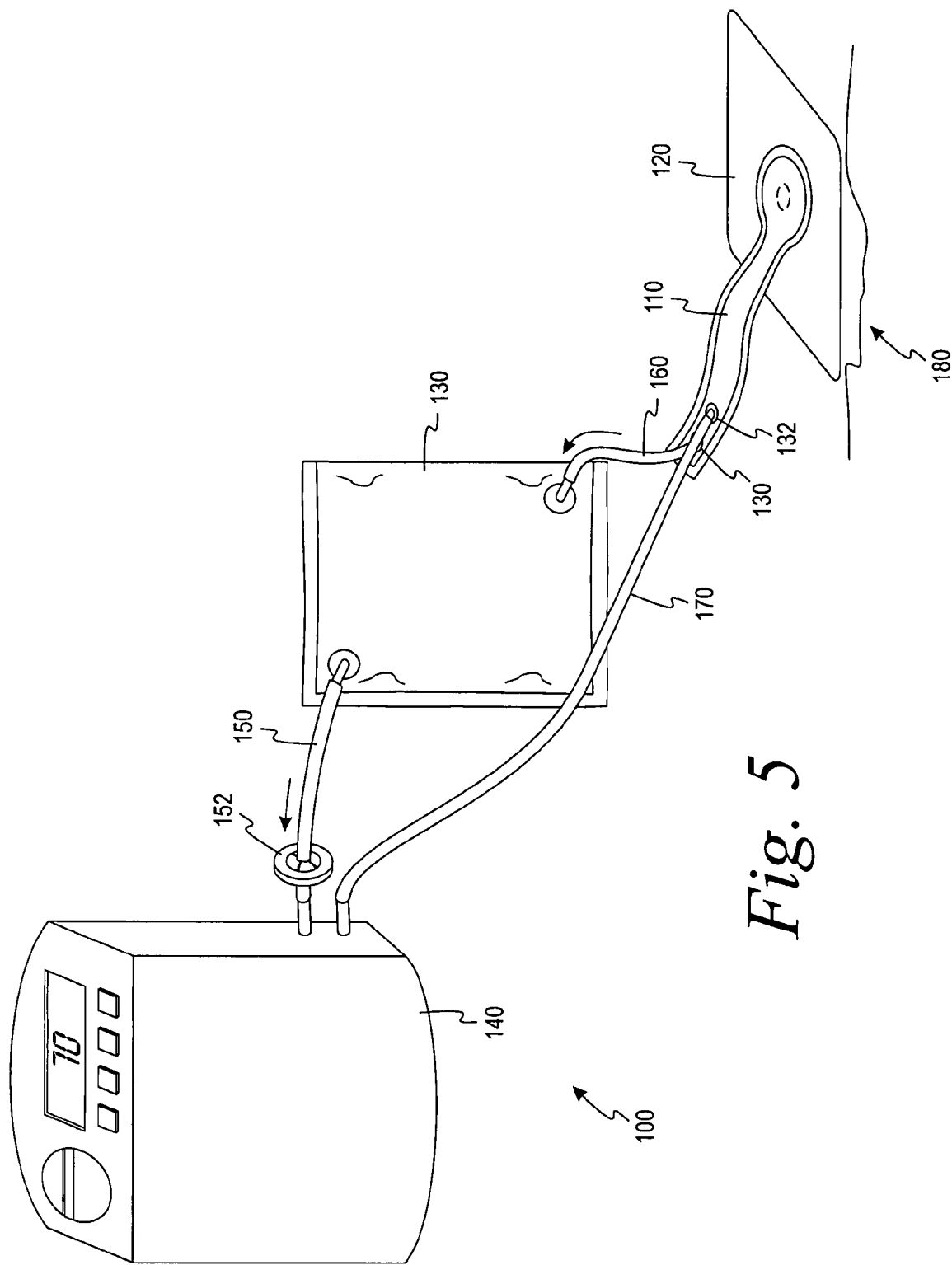
FIG. 5 illustrates a wound drainage system utilizing the flat-hose assembly.

Turning now to FIG. 5, a wound drainage system 100 is illustrated. The wound drainage system 100 has a flat-hose assembly 110 that is generally identical to the flat-hose assembly 10 previously described. The flat-hose assembly 110 is connected to a wound dressing 120. The wound dressing 120 covers a wound 180 and extends beyond the wound 180 to cover healthy skin outside of the wound 180. An adhesive (not shown), such as adhesive 24 of the flat-hose assembly 10, connects the flat-hose assembly 110 to the wound dressing 120. The wound dressing 120 may be a gel-type dressing, such as that described in U.S. patent application Ser. No. 10/909,222 which is incorporated herein by reference in its entirety. The wound dressing 120 shown in FIG. 5 is generally square with side approximately 6 inches long. Although a generally square wound dressing 120 is shown, any shape and size wound dressing suitable for covering a wound area may be used.

Another gel-type dressing is ELASTO GEL® manufactured by Southwest Technologies of Kansas City, Mo. A gel-type dressing may be advantageous as a good seal forms between the dressing and a wound with a gel-type wound dressing. Additionally, the flexibility of a gel-type wound dressing reduces the likelihood of pressure points on a patient. Gel-type wound dressings are typically impermeable to air, but absorb moisture. Gel-type wound dressings also allow a healthcare provider to remove and reattach the same wound dressing several times due to the ability of the gel material to adhere to the patient's skin.

The flat-hose assembly 110 is also connected to a collection bag 130. A controller 140 includes a vacuum pump, which applies negative pressure to the collection bag 130. During operation, exudates are drawn from a wound 180 through the wound dressing 120 and into the flat-hose assembly 110 and the exudates are deposited in the collection bag 130. The negative pressure from the controller 140 is applied to the collection bag 130 via a first tube 150. A hydrophobic filter 152 is placed on the first tube 150 to prevent any liquid from entering the controller 140. When liquid reaches the hydrophobic filter 152 the flow of the liquid is stopped, increasing the pressure in the first tube 150 between the hydrophobic filter 152 and the controller 140. The controller 140 detects the increase in pressure and turns off the negative pressure.

The first tube 150 provides negative pressure to the collection bag 130, which in turn provides negative pressure to the wound site via a second tube 160 to the flat-hose assembly 110. The second tube 160 connects to a first hose fitting of the flat-hose assembly 110 to the collection bag 130.

A third tube 170 connects to the controller 140 at one end and connects to a second fitting 132 of the flat-hose assembly 110 at an opposing end. This third tube 170 senses pressure at the wound site via the flat-hose assembly 110. This sensing capability permits the controller to control the negative pressure and allows for modulation of the negative pressure. Modulation varies the pressure from, for example, a low pressure of 1 mm Hg to a high pressure of 250 mm Hg over pre-selected intervals.

It is further contemplated that according to yet an additional embodiment that multiple flat-hose assemblies may be used on a single wound dressing on a single wound. Such an embodiment would be similar to the wound drainage system 100 shown in FIG. 5, however, at least a second flat-hose assembly would be present. It is contemplated that additional flat-hose assemblies may use the same collection bag and controller as the first flat-hose assembly. It is further contemplated that the additional flat-hose assemblies may use a separate collection bag and a separate controller than the first-flat hose assembly.

It is additionally contemplated according to yet a further embodiment that multiple flat-hose assemblies may be used on a plurality of wound dressings on a single wound. Such an embodiment would be similar to the wound drainage system 100 shown in FIG. 5, however, at least a second wound dressing and a second flat-hose assembly would be present. It is contemplated that additional flat-hose assemblies may use the same collection bag and controller as the first flat-hose assembly. It is further contemplated that the additional flat-hose assemblies may use a separate collection bag and a separate controller than the first-flat hose assembly.

While particular embodiments and applications of the present invention have been illustrated and described, it is to be understood that the invention is not limited to the precise construction and compositions disclosed herein and that various modifications, changes, and variations may be apparent from the foregoing descriptions without departing from the spirit and scope of the invention as defined in the appended claims.

What is claimed is:

1. A flat-hose assembly having a proximal end and a distal end adapted for use with a negative pressure wound drainage system, the flat-hose assembly comprising:
   a top layer;
   a bottom layer forming an opening at the distal end of the flat-hose assembly allowing exudates of a wound to flow into the flat-hose assembly; and
   a filter layer disposed between the top layer and the bottom layer, the filter layer including pores that allow the exudates to flow through the filter layer and between the bottom layer and the top layer;
   wherein the top and bottom layer form a seal area along a periphery of the top layer and the bottom layer sealing the filter layer therebetween.

2. The flat-hose assembly of claim 1 further comprising:
   a first hose fitting protruding through a first opening formed in the proximal end of the top layer; and
   a second hose fitting protruding through a second opening formed in the proximal end of the top layer.

3. The flat-hose assembly of claim 1 further comprising:
   an adhesive applied about the opening of the bottom layer, the adhesive adapted to connect the flat-hose assembly to a wound dressing of the wound drainage system.

4. The flat-hose assembly of claim 3 further comprising:
   a protective backing covering the adhesive preventing unintentional exposure of the adhesive, the protective backing being removable to expose the adhesive prior to use of the flat-hose assembly with the negative pressure wound drainage system.

5. The flat-hose assembly of claim 3, wherein the adhesive forms an airtight connection between the flat-hose assembly and the wound dressing.

6. The flat-hose assembly of claim 1, wherein the top layer and the bottom layer are a polymeric material.

7. The flat-hose assembly of claim 1, wherein the top layer and the bottom layer are generally transparent.

8. The flat-hose assembly of claim 1, wherein the top layer and the bottom layer are generally translucent.

9. The flat-hose assembly of claim 1, wherein the top layer and the bottom layer are a flexible polymeric material.

10. The flat-hose assembly of claim 1, wherein the seal between the top layer and the bottom layer is an RF weld seal, an adhesive seal, or a heat seal.

11. The flat-hose assembly of claim 1, wherein the filter layer traps particles of exudates draining from a wound within the flat-hose assembly.

12. The flat-hose assembly of claim 1, wherein the filter layer comprises a porous material selected from the group consisting of cotton, polymeric fibers, and filter screen material.

13. The flat-hose assembly of claim 1, wherein the filter layer spaces the top layer from the bottom layer, preventing the top layer from generally contacting the bottom layer beyond the seal area and thereby blocking the flow of exudates.

14. The flat-hose assembly of claim 1, wherein the distal end has a larger surface area than the proximal end.

15. A flat-hose assembly adapted for use with a negative pressure wound drainage system, the flat-hose assembly having a proximal end and a distal end and comprising:
   a top layer forming a first opening and a second opening therethrough at the proximal end of the top layer, the openings being adapted to apply negative pressure to the flat-hose assembly;
   a bottom layer forming a third opening at the distal end of the bottom layer, the third opening allowing exudates of a wound to flow into the flat-hose assembly;
   a filter layer disposed between the top layer and the bottom layer, the filter layer being adapted to prevent contact between the top layer and the bottom layer other than at a periphery of the top layer and the bottom layer, the filter layer including pores that allow the exudates to flow through the filter layer and between the bottom layer and the top layer, the filter layer further adapted to trap large particles of exudates from a wound within the flat-hose assembly, the top layer and the bottom layer forming a seal area along a periphery of the top layer and the bottom layer sealing the filter layer therebetween;
   a first hose fitting protruding through a first opening formed in the distal end of the top layer adapted to connect the flat-hose assembly to the negative pressure wound drainage system;
   a second hose fitting protruding through a second opening formed in the distal end of the top layer adapted to connect the flat-hose assembly to the negative pressure wound drainage system; and
   an adhesive adapted to connect the flat-hose assembly to a wound dressing of the wound drainage system.

16. The flat-hose assembly of claim 15, further comprising a protective backing covering the adhesive preventing unintentional exposure of the adhesive, the protective backing being removable to expose the adhesive prior to use of the flat-hose assembly with the negative pressure wound drainage system.

17. The flat-hose assembly of claim 15, wherein the seal between the top layer and the bottom layer is a RF weld seal.

18. The flat-hose assembly of claim 15, wherein the top layer and the bottom layer are generally transparent.

* * * * *